United States Patent [19]

Varco et al.

[11] Patent Number: 4,567,040

[45] Date of Patent: Jan. 28, 1986

[54] STABILIZED HAIR SPRAY COMPOSITION AND PROCESS

[75] Inventors: Joseph J. Varco, Fairfield; Carl E. Williams, Stratford, both of Conn.

[73] Assignee: Clairol Incorporated, New York, N.Y.

[21] Appl. No.: 696,852

[22] Filed: Jan. 30, 1985

Related U.S. Application Data

[63] Continuation of Ser. No. 313,093, Oct. 19, 1981, abandoned.

[51] Int. Cl.$^4$ .................. A61K 7/11; A61K 7/135
[52] U.S. Cl. .................. 424/70; 424/DIG. 1; 424/47; 424/62; 524/185; 524/388; 524/404; 549/478
[58] Field of Search .................. 424/DIG. 1, 47, 62, 424/70; 549/478; 524/185, 388, 404

[56] References Cited

U.S. PATENT DOCUMENTS

| | | | |
|---|---|---|---|
| 2,957,023 | 10/1960 | Dimler et al. | 524/296 |
| 3,193,521 | 7/1965 | Jasehing | 524/84 |
| 3,207,790 | 9/1965 | Glew et al. | 564/497 |
| 3,230,225 | 1/1966 | Arrigo | 546/351 |
| 3,372,140 | 3/1968 | Witt | 524/185 |
| 3,382,208 | 5/1968 | Cyba | 524/185 |
| 3,413,260 | 11/1968 | Arrigo | 524/185 |
| 3,415,776 | 12/1968 | White | 524/99 |
| 3,922,341 | 11/1975 | Abegg et al. | 424/78 |
| 4,164,562 | 8/1979 | Nandagiri et al. | 424/DIG. 1 |

*Primary Examiner*—Dale R. Ore
*Attorney, Agent, or Firm*—Gabriel P. Katona

[57] ABSTRACT

A hair spray composition comprising an alcoholic solution of partially neutralized vinyl/maleic copolymer and an alkali metal borohydride or oxidizer stabilized against discoloration.

8 Claims, No Drawings

STABILIZED HAIR SPRAY COMPOSITION AND PROCESS

This is a continuing application of application Ser. No. 313,093, filed Oct. 19, 1981, now abandoned.

DESCRIPTION

Field of the Invention

This application relates to improved hair spray compositions and to processes for improving the stability of hair spray compositions.

BACKGROUND OF THE INVENTION

It is important that hair spray compositions have good holding ability for the curl without giving a harsh, brittle feeling to the hair. Furthermore, the hair spray should be water soluble so that it can be washed out of the hair at the time it is shampooed.

The most commonly employed polymer ingredient of hair sprays is a copolymer of methyl vinyl ether with maleic acid or maleic anhydride. These polymers are not water soluble.

Since water solubility is a desired feature of hair sprays, the resin is partially neutralized by reacting the free carboxylic groups of the polymer with a base, such as ammonia, dimethylamine, diethylamine, diethanolamine, triethanolamine, triisopropanolamine, 2-methyl-2-amino-1-propanol, and the like. Most commercial hair sprays, whether dispensed from pressurized aerosol containers or from manual pump dispensers, are of the aforementioned type. Typical compositions of this type are described, for example, in U.S. Pat. Nos. 3,922,341 and 4,164,562.

Whereas, the alcoholic solutions of the copolymer are considered stable and have relatively good shelf life, the solutions of the partially neutralized copolymer tend to darken upon standing at room temperature within a few months and much faster at elevated temperatures. The rate of the discoloration of the initially clear solution of the partially neutralized resin, and the intensity of the discoloration depends on the particular base that is employed for neutralization. Although the discoloration can be substantially reduced by the use of different neutralizing bases, the requirement of good curl-holding ability of the ultimate product often compels the use of certain neutralizing base compounds which result in a more pronounced darkening effect than can be obtained with some other bases.

A number of other polymers were neutralized with aminomethylpropanol, including an octylacrylamide/acrylates/butylaminoethyl/methacrylate copolymer (this is a CTFA name, according to the CTFA Cosmetic Ingredient Dictionary 1977) and sold under the name Amphomer by the National Starch Co.; polyvinylpyrrilydone; and a polyvinylpyrrilydone/polyvinylacetate copolymer. None of these resins presented any discoloration problem either in their original form, or in an alcoholic solution; or in their partially neutralized form. Therefore, it appears that the special discoloration problem which we found is peculiar only to solutions of the specific partially neutralized vinyl ether/maleic acid copolymers which are most frequently used in hair sprays.

In view of the unappealing discoloration of hair sprays, products of this type have been heretofore sold in opaque aerosol or manual pump dispensing containers. It has become desireable, however, for marketing reasons, to eliminate the darkening of the neutralized resin solutions upon standing so that a commercially useful hair spray product can be obtained which can be packaged and sold in clear bottles without the development of unappealing discoloration.

SUMMARY OF THE INVENTION

In accordance with our present invention a hair spray composition was developed which retains the good curl holding ability of compositions known from the prior art as well as the absence of harshness and brittleness to the fuel, but which will not develop perceptible or objectionable discoloration upon standing even at elevated ambient temperatures to which such hair spray could become exposed, by incorporating in the composition, which contains an alcoholic solution of partially neutralized vinyl/maleic copolymer an amount of an alkali metal borohydride or of an oxidizer, effective to prevent such discoloration. In practice it was found that with the usual concentrations of the neutralizing base and the degree of neutralization, from about 0.01% to about 0.05% of the alkali metal borohydride or from about 0.4% to about 1.5% of the oxidizer, expressed as $H_2O_2$, will be effective to accomplish the desired objective.

SUMMARY OF THE PRIOR ART

Various boron compounds have been proposed for preserving solid polymers, usually olefin polymers, against weathering. Accordingly, in U.S. Pat. No. 3,382,208 the borate of N,N-di-cycloalkylalkanolamide or of N,N-di-sec-octylethanolamide is suggested to preserve a solid polyolefin against weathering. In U.S. Pat. No. 3,372,140 a $C_1$–$C_{20}$ alkyl, cycloalkyl or arylborane is disclosed for stabilizing solid olefin polymers. U.S. Pat. No. 3,193,521 discloses the stabilization of solid monolefin polymers with monohydrocarbon or heterocyclic boronic acids or their boroxole trimers. U.S. Pat. No. 3,413,260 employs a stabilizing concentration of a soluble quarternary ammonium borohydride for use in solid polymers; and U.S. Pat. No. 3,415,776 suggests stabilizing solid vinyl polymers against discoloration with a reaction product of a borane and triarylmethane dyes. U.S. Pat. No. 2,957,023 suggests dissolving an alkali metal borohydride in water, isopropanol, ethanol or low molecular weight amine, etc. solvent to stabilize higher molecular weight oxoalcohols in which the borohydrate is insoluble, to obtain improved plasticizer esters which will not discolor due to the presence of contaminants during the harsh conditions of the esterification reaction. U.S. Pat. No. 3,207,790 adds an alkali metal borohydride to reduce color formation of alkanolamines prepared from reaction of alkylene oxide with ammonia or an amine. U.S. Pat. No. 3,230,225 adds a soluble quarternary ammonium borohydride to retard polymerization of an unsaturated monomer with ethylenic linkage, such as styrene.

Accordingly, there is no recognition in the prior art of the fact that while alcoholic solutions of copolymers of maleic acid or maleic anhydride with vinyl methyl ether do not present any problem of discoloration on standing, their partially neutralized solutions would result in a color formation problem. Furthermore, there is even less of a recognition or suggestion in the prior art that the discoloration problem presented at particular partially neutralized copolymer solution can be prevented by the addition of an effective amount of an alkali metal borohydride or of an oxidizer.

As it also appears from the above survey from the prior art, the recognition of this discoloration problem as well as its solution is unique in the field of hair sprays and related resin solutions, especially at the low levels of resin concentrations employed in hair sprays.

DETAILED DESCRIPTION OF THE INVENTION

Hair holding sprays which are based on the copolymers of lower alkyl vinyl ethers with maleic acid or anhydride in the form of its ethyl or butyl monoester have been found to be particularly useful for spraying onto hair to hold the shape of the hairdo under a variety of conditions. Copolymers of this type can be represented by the structural formula:

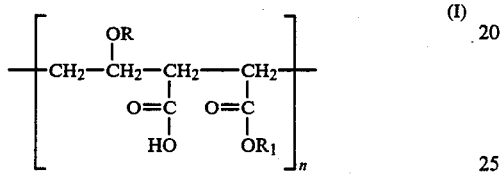

Wherein R is hydrogen or a $C_1$–$C_4$ aliphatic radical; $R_1$ is an ethyl or butyl moiety and n is a cardinal number proportional to molecular weight. The copolymers most commonly employed in hair sprays, and the ones that we have worked with, are those in which R is methyl, but we would expect that resins with the other substituents for R would behave in a similar manner when used in accordance with this invention. A resin in which R is methyl and $R_1$ is an ethyl moiety is sold under the trade name Gantrez-ES-225, and a copolymer in which R is methyl and $R_1$ is a butyl moiety is sold under the trade name Gantrez-ES-425, both by GAF Corporation, usually as a 50% solution in ethanol or isopropanol. These polymers are not water soluble. Polymers of this type are usually obtained by conventional copolymerization methods such as described in German Patent No. 571,665 and have a molecular weight usually between 15,000 and 60,000.

Since it is required of a hair spray that it should be water soluble so that it can be washed off the hair, part of the free carboxylic acid functions of the copolymer are customarily neutralized by using suitably an organic base. Approximately 10–35% of the free carboxylic acid functions of the polymer are neutralized to impart water solubility, depending on the identity of the substituents R and $R_1$. If the number of neutralized carboxylic acid functions is too low then the resulting polymer would have insufficient water solubility, while if the number of free carboxylic acid functions that is neutralized is too large then the solution may become unstable over a longer period of time in that it might form a precipitate. The desirable degree of neutralization for any given copolymer can be determined by routine experimentation as is well known in the art.

Neutralization can be accomplished with ammonia or a suitable organic base such as dimethylamine, diethylamine, triethanolamine, triisopropyolamine, an aminomethyl propanol such as 2-methyl-2-amino-1-propanol, aminomethyl-propanediol, and the like. However, not all of these bases are suitable since some more than others may impair the curl holding ability and other qualities of the resulting product. The suitability of a neutralizer can be determined by routine experimentation, however, 2-methyl-2-amino-1-propanol was found to be particularly suitable. In the case of a copolymer in which R is methyl and $R_1$ is ethyl and when aminomethyl propanol is employed for neutralization, then approximately 10% of the free carboxylic acid functions is most suitably neutralized and the neutralized portions of the resin are expected to have the following formula

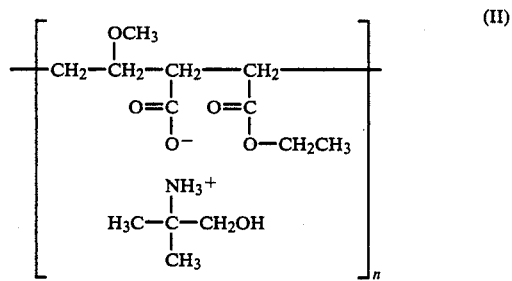

wherein n has the same meaning as above and will alternate in the appropriate proportions with the original, non-neutralized polymer moiety of Formula I. In the case of a polymer wherein R is methyl and $R_1$ is butyl it was found advantageous to neutralize about 20% of the free carboxylic acid functions.

Not only the identity of the neutralizing base but also the concentration of the copolymer and the degree of neutralization contribute of the holding character of the end product, as are all well known in the art. Accordingly, the concentration of the copolymer in the composition can be between about 0.5 and about 5% and the neutralizer constitutes about 0.05 to about 0.4%.

As used throughout the specification in the claims, all percentages are by weight, based on the entire composition, unless specified otherwise.

We do not intend to limit ourselves to a resin of the specific formula of Formula I because it has been our experience in the past that resins have often been incorrectly characterized by various manufacturers. Accordingly, in the identification of the resin we also intend to put equal weight on its definition by means of the ingredients from which it is obtained as well as on the identity of the Gantrez commercial products that are mentioned above.

The discoloration of the partially neutralized resin solution becomes noticeable when the solution stands at room temperature for about 1½ to 2½ months, and then the solution continues to darken thereafter. Higher temperatures or exposure to ultraviolet radiation accelerates the discoloration. At 50° C. the discoloration appears already within 2–3 days. The same kind of solutions stabilized with an alkali metal borohydride in accordance with this invention do not show any discoloration even after 9 months standing at room temperature. No longer exposure experience is available as yet. In the case of the solutions stabilized in accordance with our invention, standing at 50° C. results in a very slight discoloration becoming perceptible but only after about 4 months.

The employment of an oxidizer resulted in as good as, if not better, preservation of the colorless character of the partially neutralized resin solution. The presence of the oxidizer, however, resulted in a minor highlighting-type bleaching effect on the hair. This is, because, the oxidizer had to be employed, in the case of hydrogen peroxide, at a concentration between about 0.4% and about 1.5%, most suitably around 0.9% and at this concentration level a highlighting-like bleaching of the hair occurred. Accordingly, hair sprays stabilized with an oxidizer would be suitable only for rather special types of products such as a hair spray which also contributes highlighting to hair. While hydrogen peroxide is one of the suitable oxidizers that can be employed in accordance with the present invention, the term "hydrogen peroxide" as used throughout the specification and the claims is intended to include in its definition also other compounds, such as urea peroxide and alkali metal percarbonates and the like, which will act as hydrogen peroxide in aqueous medium. Obviously oxidizers which produce a colored solution, such as potassium ferricyanide cannot be employed to provide a clear hair spray in accordance with the present invention.

Other known antioxidants were also tried to be used for the purpose of color stabilization, such as propyl gallate, sucrose, dextrose, and thiourea dioxide, however it was found that when they were employed at concentration levels even considerably above 1%, the results were still unsatisfactory. Furthermore the optimum concentration in the case of alkali metal borohydrides is suitably below 0.05%.

In referring to the concentration of the alkali metal borohydride the term "effective amount", as used throughout the specification and the claims, denotes the fact that increasing the concentration of the alkali metal borohydride beyond the level of just below about 0.05% will not bring about a corresponding further improvement in the prevention of the color formation, however we do not wish to be bound by any numerical limit since an increase in the concentration of the alkali metal borohydride beyond the aforesaid optimum level will not normally be detrimental to the commercial employment of a hair spray stabilized with such higher concentrations. The use of an oxidizer instead of the alkali metal borohydride represents a different situation, because there the prevention of color formation would be coupled with the achievement of a desirable partial bleaching or highlighting effect on the hair. Accordingly, while the term "effective amount" in connection with an oxidizer indicates an amount which is effective to prevent a formation of discoloration of the solution, the term is also intended to include in its meaning concentrations of the oxidizer that may be required effectively to bring about the desired partial bleaching effect on the hair. Since, depending on the degree of desired bleaching, the concentration of the oxidizer in a given case can be higher than the minimum that would be required for prevention of color formation in the solution, the term "effective amount" as applied to the oxidizer has more than one connotation, in contrast to the single one when referring to the alkali metal borohydride.

In accordance with conventional hair spray formulation practices the spray can contain one or more alcoholic solvents, some water, a perfume, plasticizer and the like as additional ingredients.

The following examples are merely illustrative of our invention:

EXAMPLES

In all of the following examples a 5.0% $H_2O$ and 2.3% isopropanol solvent mixture was employed with 0.3% perfume and 0.2% purcellin oil as plasticizer and after calculating the amount of the copolymer resin, the neutralizer and the stabilizing component of the present invention, ethane was added to round out the concentrations to 100%. In the table below which summarizes the examples, only the concentrations of the resin, the neutralizer and that of the stabilizer component are given. As used throughout the specification and the claims the term "vinyl/maleic copolymer" is intended to denote the type of copolymers to which this invention relates and which can be represented by the type illustrated in Formula I.

In the ten Examples given in the tabulation below good stabilization against color formation was achieved in all cases and the concentrations of the particular stabilizers that were employed were determined to be the effective concentration levels at or just slightly above the optimum concentration level above which no further color inhibition can be observed. All numerical values throughout the specification and the claims are percentages by weight.

| Example | Copolymer | Copol. Conc. (Solids) | Neutralizer | Neutr. Conc. | Stabilizer | Stab. Conc. |
|---|---|---|---|---|---|---|
| 1. | Gantrez ES-225 | 4% | lithium OH | 0.075 | $NaBH_4$ | 0.01 |
| 2. | " | " | triethanolamine | 0.075 | " | 0.02 |
| 3. | " | " | aminomethyl propanol | 0.075 | " | 0.04 |
| 4. | " | " | diethanolamine | 0.075 | " | 0.05 |
| 5. | Gantrez ES-425 | 4% | lithium OH | 0.15 | " | 0.02 |
| 6. | " | " | triethanolamine | 0.15 | " | 0.04 |
| 7. | " | " | aminomethyl propanol | 0.15 | " | 0.05 |
| 8. | " | " | diethanolamine | 0.15 | " | 0.05 |
| 9. | " | " | aminomethyl propanol | 0.15 | $H_2O_2$ | 0.9 |
| 10. | Gantrez ES-225 | " | aminomethyl propanol | 0.075 | " | 0.9 |

The full scope of the invention is defined by the following claims:

We claim:

1. A hair spray composition which comprises an alcoholic solution of partially neutralized vinyl/maleic copolymer and an amount of an alkali metal borohydride, or an amount of an oxidizer, either of the aforesaid amounts being effective to stabilize said composition against discoloration.

2. The hair spray composition of claim 1, wherein said alkali metal borohydride is sodium borohydride and said effective amount is from about 0.01% to about 0.05% by weight.

3. The hair spray composition of claim 1, wherein said oxidizer comprises hydrogen peroxide and said effective amount is from about 0.4% to about 1.5%.

4. The hair spray composition of claim 1, 2 or 3 wherein said vinyl/maleic copolymer is constituted of recurring units having the formula

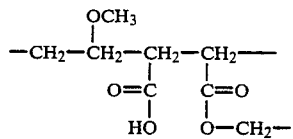 (III)

before partial neutralization and which is partially neutralized with aminomethylpropanol.

5. A process for preventing the formation of color in a partially neutralized solution of a vinyl/maleic copolymer, which comprises adding to the solution an effective amount of an alkali metal borohydride or an oxidizer that is effective to prevent such color formation.

6. The process of claim 5, wherein said alkali metal borohydride is sodium borohydride and said effective amount is from about 0.01% to about 0.05% by weight.

7. The process of claim 5, wherein from about 0.4% to about 1.5% hydrogen peroxide is employed as the oxidizer.

8. The process of claims 6 or 7 wherein said vinyl/maleic copolymer is constituted of recurring units having the formula

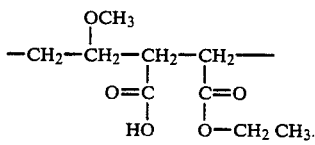 (III)

* * * * *